(12) United States Patent
Abousaleh

(10) Patent No.: US 8,366,416 B2
(45) Date of Patent: Feb. 5, 2013

(54) PUMPING DEVICE

(75) Inventor: Khaled Abousaleh, Paris (FR)

(73) Assignee: Pulssar Technologies, Gennevilliers (FR)

( * ) Notice: Subject to any disclaimer, the term of this patent is extended or adjusted under 35 U.S.C. 154(b) by 623 days.

(21) Appl. No.: 12/160,781

(22) PCT Filed: Jan. 4, 2007

(86) PCT No.: PCT/FR2007/000018
§ 371 (c)(1),
(2), (4) Date: Aug. 26, 2008

(87) PCT Pub. No.: WO2007/080300
PCT Pub. Date: Jul. 19, 2007

(65) Prior Publication Data
US 2010/0098562 A1 Apr. 22, 2010

(30) Foreign Application Priority Data
Jan. 11, 2006 (FR) ...................................... 06 00318

(51) Int. Cl.
*F04B 17/00* (2006.01)
(52) U.S. Cl. .......... 417/422; 417/63; 417/415; 417/505; 222/63; 222/333
(58) Field of Classification Search ................. 417/238, 417/63, 415, 442, 505; 340/648, 635; 422/100; 222/63, 333
See application file for complete search history.

(56) References Cited

U.S. PATENT DOCUMENTS

| | | | | |
|---|---|---|---|---|
| 3,963,148 A * | 6/1976 | Proni et al. | ..... | 222/132 |
| 5,474,744 A * | 12/1995 | Lerch | ..... | 422/510 |
| 5,707,212 A * | 1/1998 | Matthews | ..... | 417/44.1 |
| 6,460,567 B1 * | 10/2002 | Hansen et al. | ..... | 137/554 |
| 6,589,791 B1 * | 7/2003 | LaBudde et al. | ..... | 436/55 |
| 2004/0028565 A1 * | 2/2004 | Abou-Saleh et al. | ..... | 422/100 |

FOREIGN PATENT DOCUMENTS

| | | |
|---|---|---|
| FR | 2096275 | 2/1972 |
| FR | 2815719 A1 | 4/2002 |
| GB | 2055986 A | 3/1981 |
| GB | 2126117 A | 3/1984 |

* cited by examiner

*Primary Examiner* — Devon Kramer
*Assistant Examiner* — Thomas Fink
(74) *Attorney, Agent, or Firm* — Browdy and Neimark, PLLC

(57) ABSTRACT

A pumping device including a housing whose front face is at least partly formed by a block of transparent material, this block containing a number of machine-drilled holes including at least one blind hole forming a work chamber, at least one hole forming an admission and/or exhaust channel leading into the blind hole, two through channels whose orifices on the front face of the block are fitted with hydraulic hose connection means, two solenoid valves, a plunger sliding leaktightly in a bearing fitted to the orifice of the blind hole, this plunger defining with the blind hole a volume that varies as a function of the axial position of the plunger, and a module connected to the base of the plunger for moving the plunger translationally. The pumping device can be used for pipetting, dilution, rinsing and/or dispensing of samples, regardless of the envisaged volume ranges.

12 Claims, 5 Drawing Sheets

PUMPING DEVICE

BACKGROUND OF THE INVENTION

1. Field of the Invention

The present invention concerns a pumping device for many types of samplings. It is applicable more particularly, but not exclusively, for the pipetting, dilution, rinsing and/or distribution of samples, i.e. regardless of the volume ranges considered.

2. Background

In general, one knows that a number of devices have already been proposed making it possible to carry out pipetting and rinsing cycles, in particular within an automatic analysis device.

Through patent FR 2 815 719, we know a pipetting device using at least two work chambers, one having a small volume to take samples, the other having a large volume to perform rinsing.

Indeed, to perform various samplings with a satisfactory precision, this device requires the use of two work chambers having different volumes.

Moreover, such a device is designed to be integrated into a particular type of analysis machine. It is therefore not designed to equip apparatuses of different types or even to be used in a laboratory assembly.

However, in the latter type of application, it is desirable for the devices used to be relatively independent and to be housed in cases which are preferably shielded so as to free themselves from external influences, for example of an electromagnetic nature, or even ionizing radiation.

These apparatuses must enable the realization of fast connections of admission and/or exhaust hoses as well as a complete visualization of the hydraulic circuit so as to be able to verify the proper operation of the assembly and detect the presence of any gas bubbles or impurities.

Of course, such an apparatus must meet increasingly strict compactness criteria.

OBJECTS

The first aim of the invention is therefore the realization of a pumping device having a simple structure using only one motorization and only one work chamber, offering easy access, a compact arrangement and control of the hydraulic circuits, including the pump.

SUMMARY

In order to achieve these results, the pumping device according to the invention comprises:
- a housing whereof the front face is at least partially formed by a block of transparent material which extends partially inside the housing, this block being provided with machine-drilled holes at least one of which is a blind hole constituting a work chamber, at least one hole constituting an admission and/or exhaust channel which leads into the blind hole at the rear face of the block, two through channels each leading onto the front face and the rear face of the block, orifices of these two through channels located at the front face of the block being equipped with means for connecting hydraulic hoses,
- two solenoid valves fixed on the rear face of the block, each of these solenoid valves being connected on one hand to the admission and/or exhaust channel, and on the other hand to a corresponding one of said through channels,
- a plunger sliding leaktightly in a first bearing fitted to the orifice of the blind hole, this plunger defining, with said blind hole, a volume which varies according to the axial position of the plunger,
- a module connected to the base of the plunger for driving the plunger in translation.

Of course, the bearing may be formed to ensure sealing between the work chamber, the plunger and the rest of the pumping device.

Said bearing may, for example, comprise an O-ring joint or a double-wall crown comprising internal and external sealing joints and a base with means for fixing to the block.

The device according to the invention may comprise two holes constituting an admission channel and an exhaust channel, respectively, which lead into the blind hole at the rear face of the block and are each directly connected to one of said solenoid valves.

Said drive module may extend under the block and the solenoid valves and laterally in relation to the latter parts so as to be as compact as possible.

Said drive module may comprise a drive carriage connected to the plunger and driven in translation using a control rod meshing with a pinion moved by a motorization such as a stepping motor.

In variation, this drive carriage could be driven in translation using a worm screw, itself driven in translation by a motorization comprising a stator and an annular rotor whereof the interior surface has a threading in which the screw engages. Advantageously, this variation may make it possible to obtain an even more compact device.

Said motorization may be able to drive said drive carriage in translation with a precision corresponding to an increment defined by the drive carriage/motorization assembly.

Said hydraulic hoses may, for example, comprise pipetting means, a liquid reserve.

The through channels may be admission and/or exhaust channels.

Of course, the transparent part of the front face of the block is located at least at the level of the work chamber.

In this way, the transparency of the front face makes it possible to verify the proper operation of the pumping device, in particular the existence of undesired air bubbles or impurities in the through channels and the work chamber.

According to a first advantage, the device according to the invention may be dimensioned so as to be able to be compatible with the analysis machines currently used, but it may also be used periodically as portable equipment for different pumping operations, for example in a laboratory, and without being integrated into a specific analysis device.

Such a use is simplified by the placement of orifices for access to the through channels on the front face of the housing.

According to a second advantage, the plunger/bearing assembly may be interchangeable so as to vary the diameter of the plunger. Indeed, the variation of the volume of the work chamber depends on the axial position of the plunger, but also on the diameter of the plunger, which makes it possible to change the volume range.

The housing may comprise a removable part, for example its lower face, to allow changing of the plunger/bearing assembly.

One thereby increases the precision of the pumped volume by an adjustment smaller than one increment.

Indeed, the variation and in particular the decrease of the diameter of the plunger are an additional adjustment element.

For example, if one divides the diameter of the plunger by two, one increases the precision of the device by four, i.e. one divides the initial increment imposed by the motorization by four, or in other words one decreases the initial increment in the ratio by the square of the diameters of the plunger.

Thus, changing the plunger and the bearing makes it possible always to have a volume range accompanied by an ad hoc precision adapted to the volume of liquid to be pumped.

The solenoid valves may be two-way solenoid valves.

Said solenoid valves and said motorization may be controlled by a processor receiving information relative to the position of the plunger.

The aforementioned information may be obtained using an optical instrument connected to said drive module.

Of course, the device according to the invention may also comprise means for controlling the drive module and solenoid valves designed so as to ensure a cycle comprising at least:

an admission phase in which the first solenoid valve is open, the second solenoid valve is closed and the drive module creates a translation of the plunger so as to increase the volume of the work chamber, the volume increase of the chamber causing the aspiration of a liquid, for example in pipetting means connected to a first through channel, an exhaust phase in which the first solenoid valve is closed, the second solenoid valve is open, the drive module then acting so as to cause a reduction of the volume of said work chamber and a discharge of the sucked up liquid through a second through channel.

According to one variation, the device according to the invention may also comprise means for controlling the drive module and solenoid valves designed so as to ensure operation in bypass mode where the two solenoid valves are open.

Lastly, the structure of the housing of the device according to the invention may constitute a double electromagnetic shielding. Indeed, it makes it possible not only to free the device from influences of an electromagnetic nature outside the housing, but it also makes it possible to avoid disturbing measurements outside the housing by the appearance of electromagnetic disturbances due to the motorization and the solenoid valves of the device according to the invention.

BRIEF DESCRIPTION OF THE DRAWINGS

Embodiments of the invention will be described below, as non-limiting examples, in reference to the appended drawings in which.

DETAILED DESCRIPTION

Figure 1:
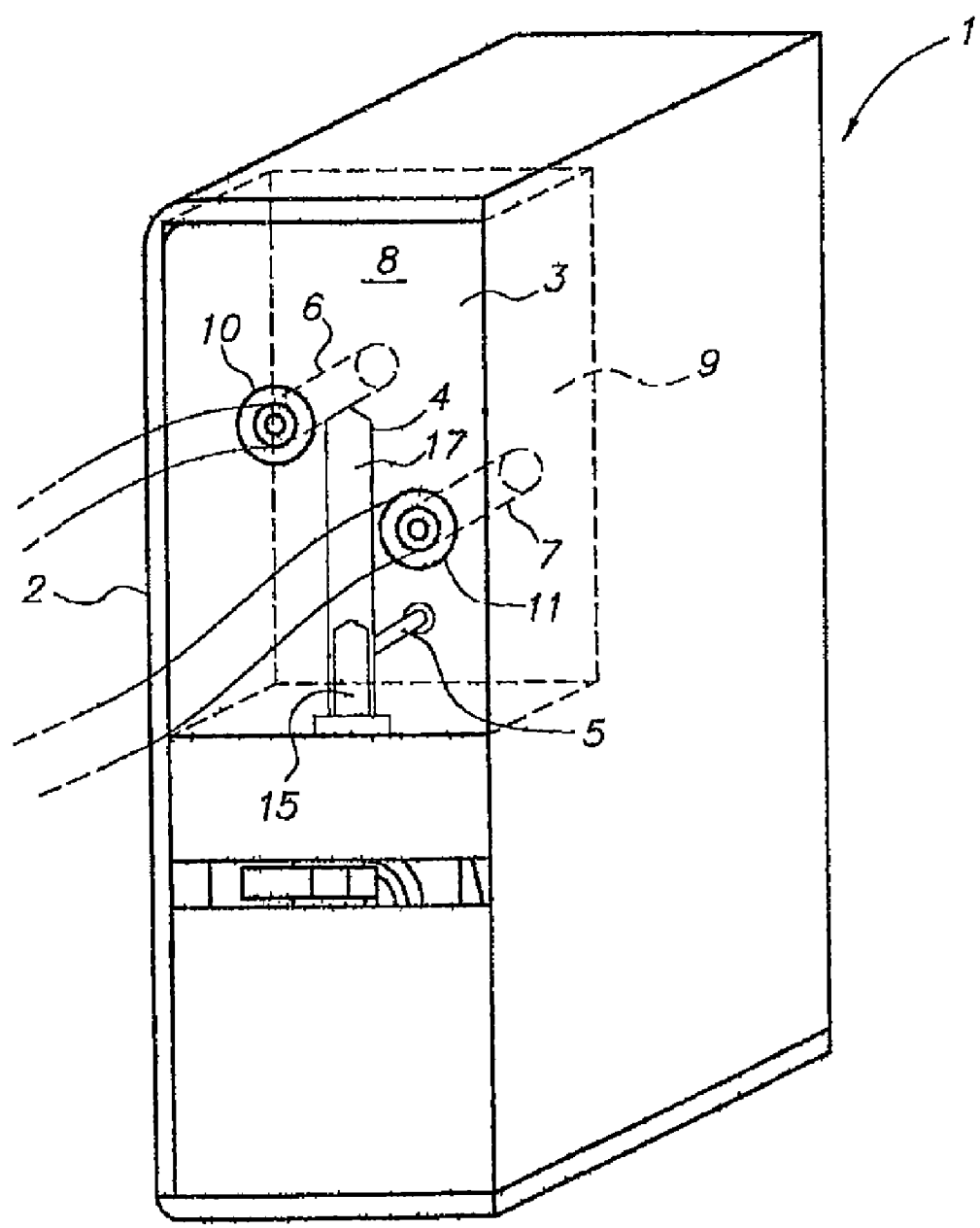
FIG. 1 is a perspective illustration of a device according to the invention.

In the example illustrated in FIG. 1, the pumping device comprises:

a housing 1 whereof the upper part of the front face 2 is formed by a block 3 of transparent material which extends partially inside the housing 1; this block 3 is provided with machine-drilled holes one of which is a blind hole 4, a hole constituting an admission and/or exhaust channel 5 which leads into the blind hole 4 at the rear face of the block, two through channels 6, 7 each leading onto the front face 8 and the rear face 9 of the block 3, orifices 10, 11 of these two through channels 6, 7 located at the front face 8 of the block 3 being equipped with means for connecting hydraulic hoses, two two-way solenoid valves 12, 13 fixed on the rear face 9 of the block 3 via a connection piece 14 extending against the rear face 9 of the block 3, each of these solenoid valves being connected on one hand to the admission and/or exhaust channel 5, and on the other hand to one of said through channels 6, 7, respectively, a plunger 15 sliding leaktightly in a bearing 16, fitted to the orifice of the blind hole 4, this plunger 15 defining, with said blind hole 4, a work chamber 17 whereof the volume varies according to the axial position of the plunger 15, a module for driving the plunger in translation, this module comprising a drive carriage 18 connected to the base of the plunger 15 and driven in translation by a control rod 19 meshing with a pinion 20 moved by a stepping motor 21.

The upper ends of the blind hole 4 and the plunger 15 are conical in a form-fitting manner.

Said bearing 16 is in the form of a crown having an L-shaped section inserted into the orifice of the blind hole 4.

It should be noted that the bearing may also have a square or rectangular section or a section of another shape which may be at least partially inserted in the orifice of the blind hole 4 and comprise, on its upper part, an O-ring joint which is compressed in a bore located at the orifice of the blind hole 4 in order to create the required sealing between the work chamber 17, the plunger 15 and the rest of the device.

It should also be noted that the plunger 15 and the bearing 16 may be interchangeable. To this end, part of the lower face of the housing may be removable in order to be able to change said plunger and said bearing and replace them with a bearing/plunger assembly having a larger or smaller diameter. The exterior diameter of the bearing is constant and the internal diameter of the bearing is equal to the external diameter of the plunger.

The solenoid valve 12 located above is in a horizontal position, the solenoid valve 13 located below is in a vertical position in order to leave a lateral space next to the solenoid valve 13 behind the block 3 for the control rod 19.

According to one variation, the connecting piece 14 not extending over the entire width of the block, said lateral space may be located at least partly next to said connecting piece.

Control of the solenoid valves 12, 13 and the motor 21 is provided by a microcontroller 22 located in the rear part of the housing. An optical sensor provides only the "zero" position of the system.

In this example, the state of the valve 12 is always opposite that of the valve 13, i.e. when the valve 12 is open, the valve 13 is closed, and vice versa.

Figure 2:
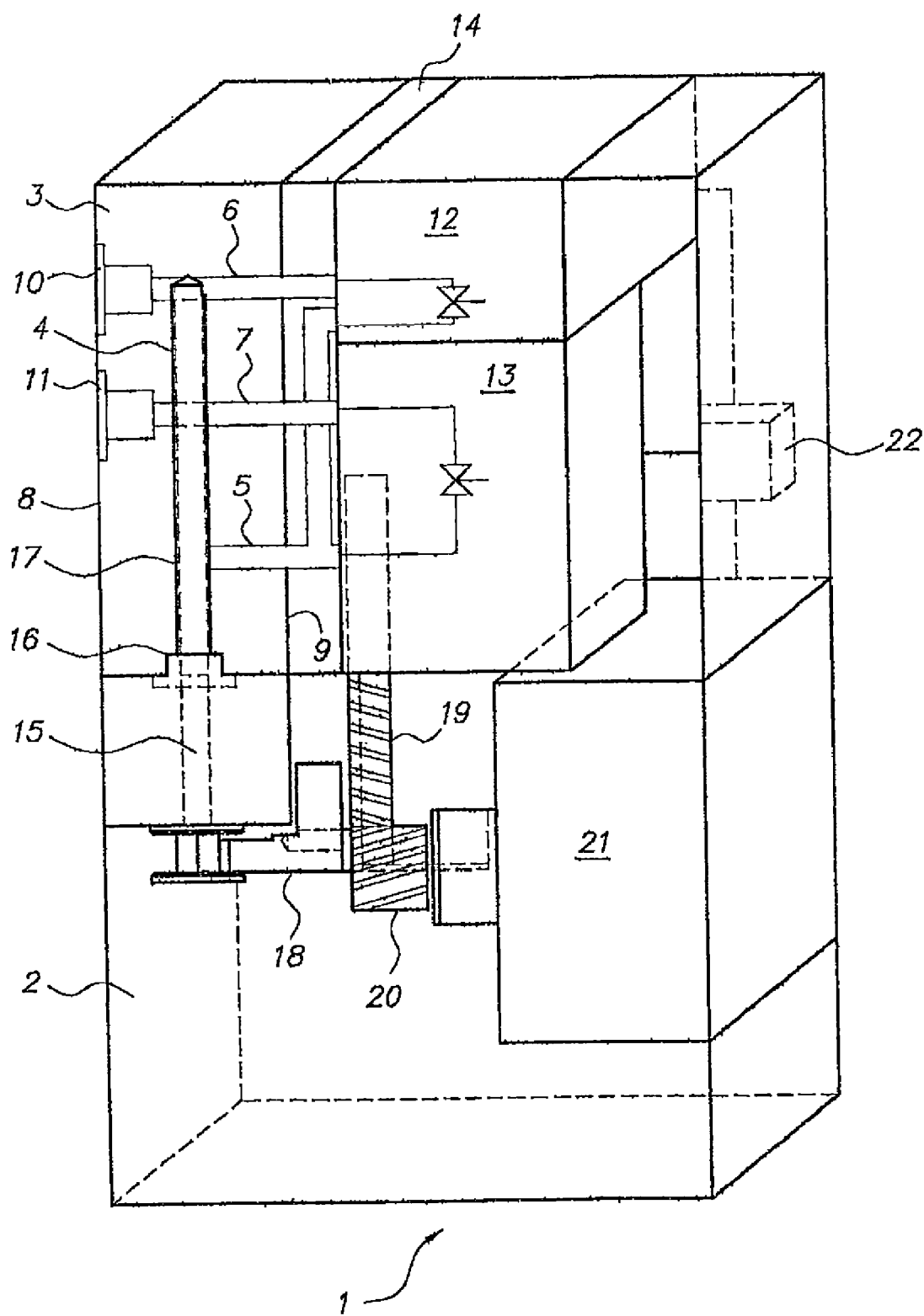
FIG. 2 is a side view of the device from FIG. 1.
Figure 3:
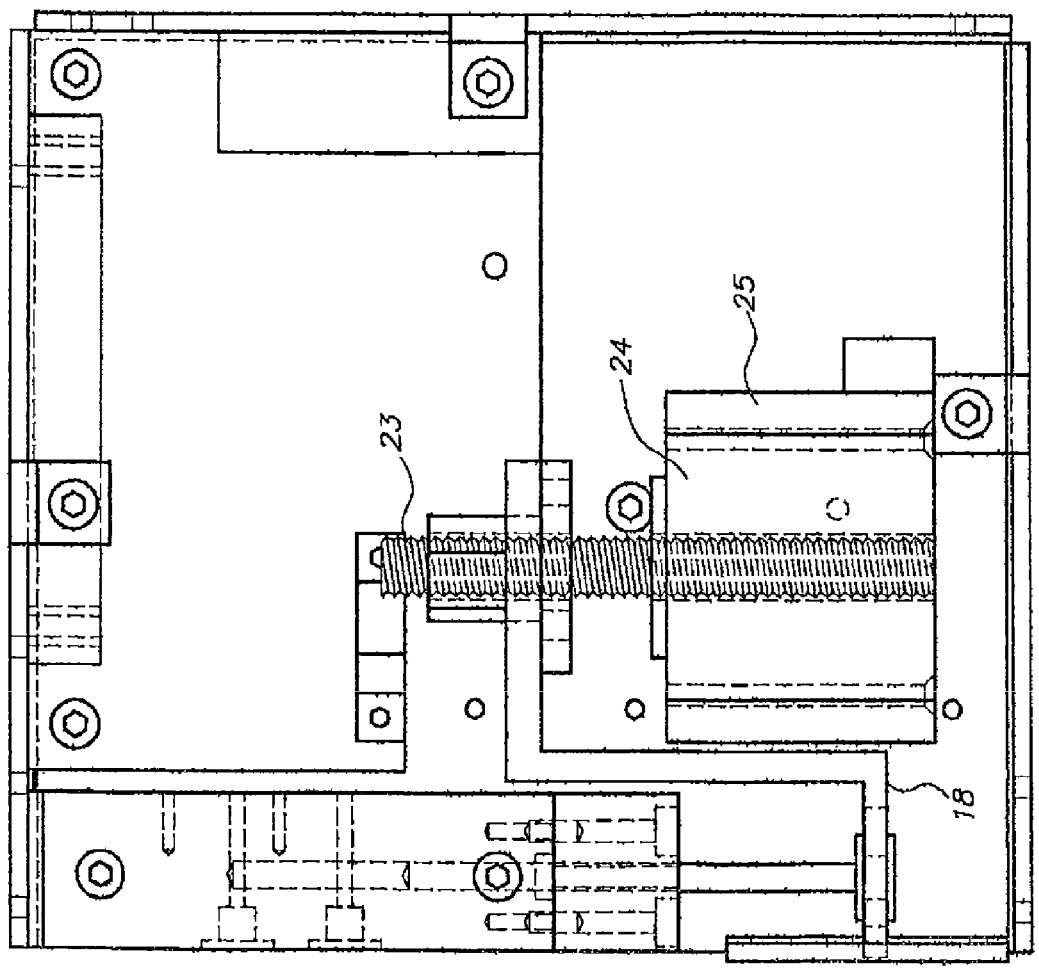
FIG. 3 is a cross-sectional view of a second device according to the invention.

Other mechanisms for driving the plunger in translation may be considered, such as a vertically-centered worm screw 23 and moved by a threaded hollow rotor 24 housed in a stator 25. Said worm screw is located in the lateral space located next to the vertical solenoid valve as in the device from FIG. 2.

Figure 4:
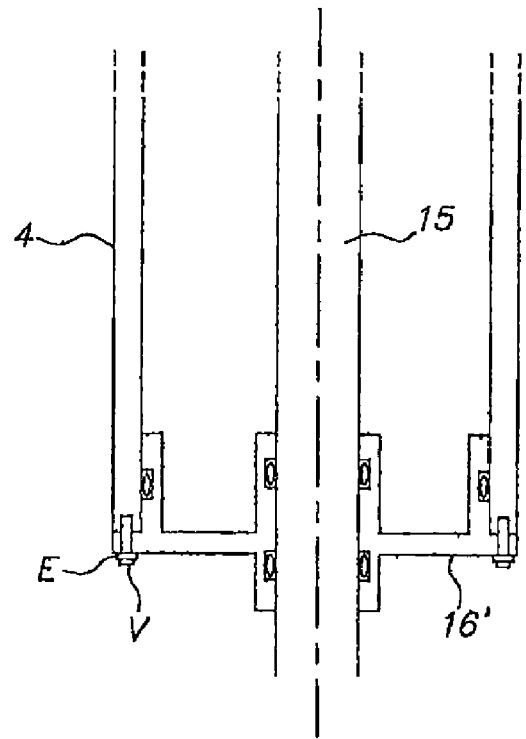
FIG. 4 is a cross-sectional illustration of the blind hole and of the plunger of a device according to the invention with a second type of interchangeable bearing.
Figure 5:
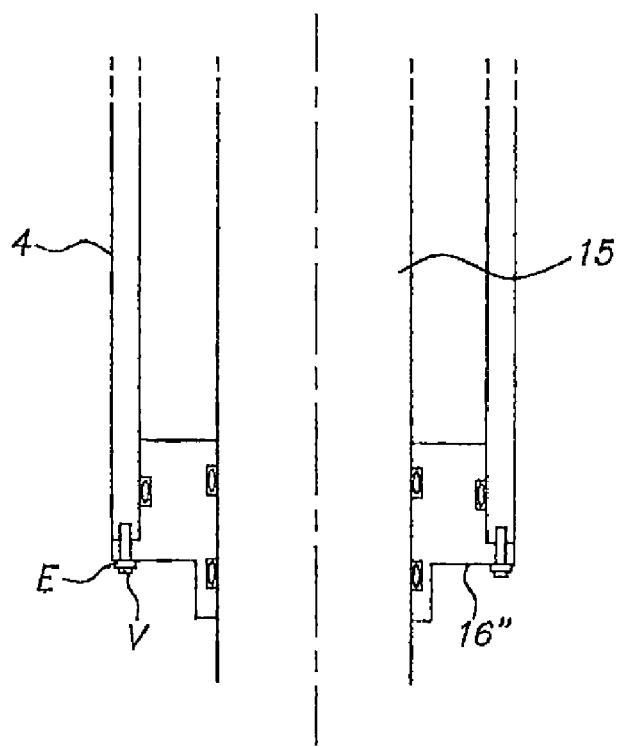
FIG. 5 is a cross-sectional illustration of the blind hole and of the plunger of a device according to the invention with a third type of interchangeable bearing.

FIGS. 4 and 5 illustrate variations of an interchangeable bearing 16' and 16" comprising a double-wall crown comprising internal and external sealing joints and a base enabling its fixing on the block, for example using a screw V/nut E assembly.

It should be noted that at the level of the passage of the plunger, the bearing may comprise teeth so as to reduce the friction of the plunger on the bearing while preserving the sealing.

Figure 6A:
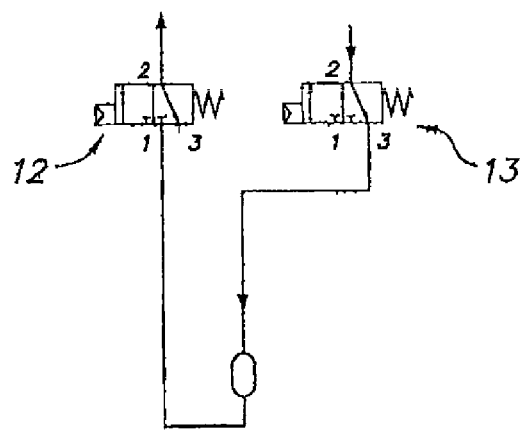
FIGS. 6a, 6b and 6c are illustrations of the fluidic circulation in a device according to the invention.
Figure 6B:
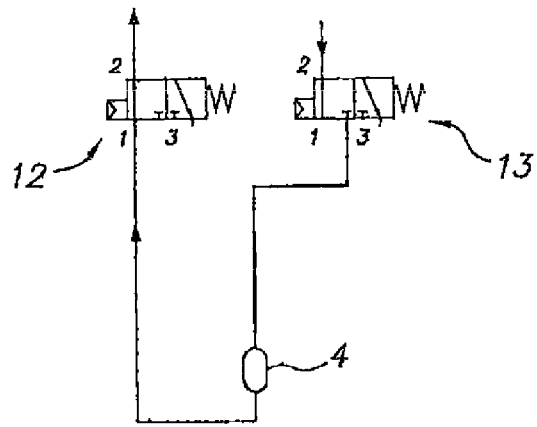
Figure 6C:
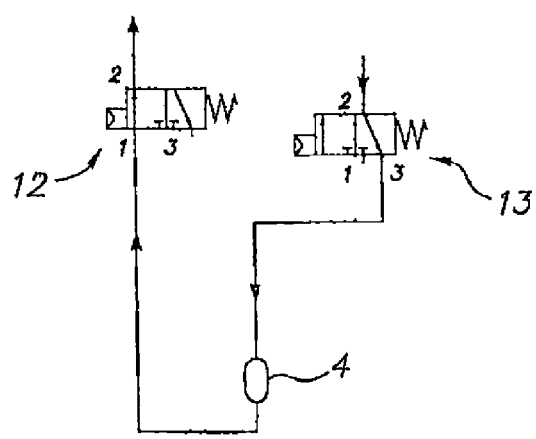

A device according to the invention may operate according to one of the following modes:

- an aspiration mode where the solenoid valve 13 is open and the solenoid valve 12 is closed (FIG. 6a), and the drive module creates a translation of the plunger so as to increase the volume of the work chamber, the growth of the chamber's volume causing the aspiration of a liquid, for example in pipetting means connected to the admission through channel 7 by the orifice 11,
- an exhaust mode where the solenoid valve 13 is closed and the solenoid valve 12 open (FIG. 6b), the drive module then acting so as to cause a reduction of the volume of said work chamber and a discharge of the sucked up liquid through the exhaust channel 6 by the orifice 10,
- a bypass mode where both solenoid valves 12 and 13 are open (FIG. 6c).

The device according to the invention may be used for applications requiring great precision, for example in a range varying from 3 µL to 5.0 mL.

The resolution is approximately 4500 increments in standard mode and 36,000 increments in microstepping mode for a plunger movement of 30 mm.

The invention claimed is:

1. A pumping device, comprising:
    a housing having a front face that is at least partially formed by a block of material which extends partially inside the housing, said block consisting of:
        a single blind hole formed in a bottom surface of the block leading to a bore in the block,
        a first hole on a rear face of the block leading to an admission channel through which fluid is input to the bore and a second hole on a rear face of the block leading to an exhaust channel through which fluid is output from the bore, both said admission channel and said exhaust channel having an end that opens into the bore, and
        two through channels each leading between a front face and the rear face of the block, each of the two through channels comprising orifices located at the front face of the block, each of the orifices being fitted with a hydraulic hose connection configured to attach hydraulic hoses to the block,
    two solenoid valves fixed on the rear face of the block, a first one said solenoid valves being connected to the admission channel and to a first one of said two through channels for controlling fluid input into the bore and a second one of said solenoid valves being connected to the exhaust channel and to a second one of said two through channels for controlling fluid out from the bore,
    a plunger sliding leaktightly in a bearing fitted to the bore, said plunger defining, with said bore, a work chamber having a volume varying according to the axial position of the plunger, and
    a module for axially driving the plunger in the bore to vary the volume, the module being connected to the base of the plunger.

2. The device according to claim 1, wherein said drive module extends under the block and the solenoid valves and laterally in relation thereto so as to be as compact as possible.

3. The device according to claim 1, wherein said drive module comprises a drive carriage connected to the plunger and driven in translation using a control rod meshing with a pinion moved by a motor.

4. The device according to claim 1, wherein said drive module comprises a drive carriage driven in translation using a worm screw, said worm screw driven in translation by a motor comprising a stator and an annular rotor whereof the interior surface has a threading in which the screw is engaged.

5. The device according to claim 1, wherein each of said hydraulic hoses is connected to at least one of a pipetting means and a liquid reserve.

6. The device according to claim 1, wherein the plunger and the bearing are interchangeable so as to vary the diameter of the plunger and always to have a volume range accompanied by an ad hoc precision adapted to the volume of the liquid to be pumped.

7. The device according to claim 1, wherein the housing comprises a removable part to allow changing of the plunger and the bearing.

8. The device according to claim 3, further comprising a processor receiving information relative to the position of the plunger and controlling said solenoid valves and said motor.

9. The device according to claim 8, wherein said information is obtained using an optical instrument connected to said drive module.

10. The device according to claim 1, further comprising means for controlling the drive module and solenoid valves designed so as to ensure a cycle comprising at least:
    one admission phase in which the first solenoid valve is open, the second solenoid valve is closed and the drive module creates a translation of the plunger so as to increase the volume of the work chamber, the increase in the volume of the chamber causing the aspiration of a liquid, into pipetting means connected to a first through channel,
    one exhaust phase in which the first solenoid valve is closed, the second solenoid valve is open, the drive module then acting so as to cause a reduction of the volume of said work chamber and a discharge of the sucked up liquid through a second through channel.

11. The device according to claim 1, further comprising means for controlling the drive module and solenoid valves designed so as to ensure operation in bypass mode where both solenoid valves are open.

12. The device according to claim 1, wherein the holes are machined-drilled.

* * * * *